United States Patent [19]

Onopchenko et al.

[11] 4,102,919

[45] Jul. 25, 1978

[54] ISOMERIC DICARBOXY, DI (HYDROXYMETHYL), DIPHENYLMETHANES AS NEW COMPOUNDS

[75] Inventors: Anatoli Onopchenko, Monroeville; Johann G. Schulz, Pittsburgh; Edward T. Sabourin, Allison Park, all of Pa.

[73] Assignee: Gulf Research & Development Company, Pittsburgh, Pa.

[21] Appl. No.: 748,687

[22] Filed: Dec. 8, 1976

[51] Int. Cl.$^2$ .............................................. C07C 65/14
[52] U.S. Cl. ............................... 260/520 E; 260/343.6
[58] Field of Search ...................................... 260/520 E

[56] References Cited

FOREIGN PATENT DOCUMENTS 835,049  1/1961  France.

Primary Examiner—Paul J. Killos

[57] ABSTRACT

Isomeric dicarboxy, di(hydroxymethyl), diphenylmethanes as new compounds.

4 Claims, No Drawings

ISOMERIC DICARBOXY, DI (HYDROXYMETHYL), DIPHENYLMETHANES AS NEW COMPOUNDS

BACKGROUND OF THE INVENTION

1. Field of the Invention

This invention relates to isomeric dicarboxy, di(hydroxymethyl), diphenylmethanes as new compounds.

2. Description of the Prior Art

The art does not disclose isomeric dicarboxy, di(hydroxymethyl) diphenylmethanes claimed herein.

SUMMARY OF THE INVENTION

The specific novel isomeric dicarboxy, di(hydroxymethyl), diphenylmethanes claimed herein can be defined as follows:

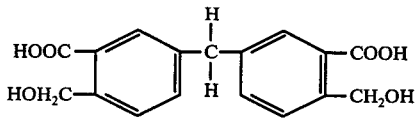

[3,3'-dicarboxy, 4,4'-di(hydroxymethyl), diphenylmethane],

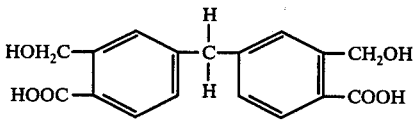

[4,4'-dicarboxy, 3,3'-di(hydroxymethyl), diphenylmethane], and

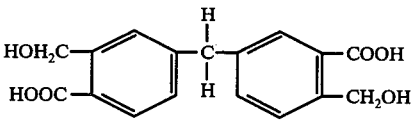

[4,3'-dicarboxy, 3,4'-di(hydroxymethyl), diphenylmethane].

BRIEF DESCRIPTION OF PREPARATION OF NEW COMPOUNDS

The new compounds claimed herein, namely, 3,3'-dicarboxy, 4,4'-di(hydroxymethyl), diphenylmethane, 4,4'-dicarboxy, 3,3'-di(hydroxymethyl), diphenylmethane and 4,3'-dicarboxy, 3,4'-di(hydroxymethyl), diphenylmethane are obtained by converting, respectively, 3,3'-dicarboxy, 4,4'-di(hydroxymethyl), diphenylmethane dilactone, 4,4'-dicarboxy, 3,3'-di(hydroxymethyl), diphenylmethane dilactone and 4,3'-dicarboxy, 3,4'-di(hydroxymethyl), diphenylmethane dilactone disclosed and claimed in our copending application Ser. No. 748,686, entitled Process for Preparing Novel Dicarboxy, di(hydroxymethyl), Diphenylmethane Dilactones filed concurrently herewith.

In accordance with our copending application defined above, which is incorporated herein by reference, the specific dilactone defined above are obtained by subjecting benzophenone-3,4,3',4'-tetracarboxylic dianhydride to hydrogenation in a hydrogen atmosphere using an ether or ester carrier in the presence of a hydrogenation catalyst pretreated in a hydrogen atmosphere.

In preparing the novel dicarboxy, di(hydroxymethyl), diphenylmethanes claimed herein, any or combination of the specific dilactones defined and claimed in our said copending application, is first treated with an aqueous alkali metal hydroxide solution, such as from about 0.5 to about 60, preferably from about five to about 25%, sodium or potassium hydroxide solution in an amount at least stoichiometrically required to react with the ester portions of said dilactones. This is done by stirring a mixture of said dilactone or dilactones and said alkali metal hydroxide at a temperature of about 20° to about 200° C., preferably about 50° to about 100° C., and a pressure of about atmospheric to about 200 pounds per square inch gauge (about 13.6 kilograms per square inch gauge), or higher, preferably atmospheric, for about 10 minutes to about six hours, preferably about 15 minutes to about one hour. As a result of such reaction the alkali metal salt corresponding to the dilactone used is obtained. The solution is then acidified by adding a suitable acid thereto, such as hydrochloric acid, until the solution is neutral to litmus paper. At this point, the novel dicarboxy, di (hydroxymethyl), diphenylmethanes claimed herein will precipitate out of solution and are recovered therefrom by simple filtration. The precipitate is then washed with water, and air or vacuum oven dried, for example at room temperature, to remove any volatile solvents adhering thereto.

DESCRIPTION OF PREFERRED EMBODIMENTS

EXAMPLE I

A slurry containing 15 grams of nickel catalyst (Ni-0104P, manufactured by Harshaw Chemical Company, Cleveland, Ohio) and 500 milliliters of tetrahydrofuran was stirred under a hydrogen atmosphere of 1000 pounds per square inch gauge (68 kilograms per square centimeter) at a temperature of 190° C. for 30 minutes.

A slurry containing 150 grams of benzophenone-3,4,3',4'-tetracarboxylic dianhydride, 15 grams of nickel, treated as above, and 500 milliliters of tetrahydrofuran was then stirred under a hydrogen atmosphere of 1050 pounds per square inch gauge (71.4 kilograms per square centimeter) at a temperature of 200° C. for 30 minutes. At the end of the reaction, the reaction mixture was cooled to room temperature depressured to atmospheric pressure and then filtered to separate nickel and unreacted benzophenone-3,4,3',4'-tetracarboxylic dianhydride therefrom. The filtrate obtained was then concentrated to about one-third its volume by heating in a rotary filter and the crystalline product that formed was recovered by filtration and twice crystallized from ethyl acetate to further purify the same. The amount of crystalline material recovered amounted to 54.8 grams. NMR and IR studies of the crystalline material disclosed the presence of the following three dilactones: 3,3'-dicarboxy, 4,4'-di(hydroxymethyl), diphenylmethane dilactone, 4,4'-dicarboxy, 3,3'-di(hydroxymethyl), diphenylmethane dilactone and 4,3'-dicarboxy, 3,4'-di(hydroxymethyl), diphenylmethane dilactone. Neutral equivalent determinations for the dilactones, $C_{17}H_{12}O_4$, was 145, substantially in agreement with theoretical, 140. Carbon and hydrogen analysis of the dilactones was found to be 72.42 percent and 4.50 percent, respectively, substantially in agreement with the theoretical values of 72.85 percent and 4.32 percent, respectively. The melting point of the dilactones was 182° to 184° C.

Several attempts were made made to determine isomeric composition of the dilactone charge used herein to produce the novel diphenylmethane claimed herein using gas chromatography but without success. Therefore, a sample of product was subjected to hydrogenolysis following the procedure of N. Finch et al in the Journal of Organic Chemistry, Volume 41, No. 15, page 2509 (1976), resulting in an acidic product having a neutral equivalent of 158.6 and a melting point range of 50° –82° C. (theoretical neutral equivalent = 142). Gas chromatographic analysis of the dimethyl, diphenylmethane, dicarboxylic acids gave three major components in 20.9, 43.5 and 35.6 weight percent, respectively, in order of their appearance on the chromatogram, accounting for over 95 percent of the total product. No attempts were made to determine which peak on the chromatogram corresponded to which isomer. The products of hydrogenolysis are 3,3'-dimethyl-4,4'-dicarboxydiphenylmethane, 3,3'-dicarboxy-4,4'-dimethyldiphenylmethane and 3,4'-dimethyl-4,3'-dicarboxydiphenylmethane, each corresponding to the respective dilactone isomer. To show that no unusual rearrangements have occurred during dilactone preparation, a portion of the product was oxidized with 25 percent nitric acid at 175° –180° C., resulting in a recovery of 79 percent yield of a known 3,4,3',4'-benzophenone tetracarboxylic acid, identical in all respects to the authentic sample.

A mixture containing 20 grams of the dilactone mixture obtained above and 10 percent molar excess of five percent aqueous sodium hydroxide was stirred while heating at a temperature of 100° C. for 30 minutes until substantial solution was obtained. The reaction mixture was filtered to remove a small amount (about 0.2 gram) of undissolved material and, while stirring, the filtrate was acidified with concentrated hydrochloric acid until the resulting solution was neutral to litmus paper. The solution was concentrated on a rotary evaporator, filtered and the white solids that were recovered were washed several times with 100-milliliter portions of water. The solids were air dried for six hours and then further dried in a vacuum oven at 60° for 24 hours. A total of 21.7 grams of product was recovered, amounting to a yield of 97 percent. IR analysis of the solid product showed the presence of carboxyl and hydroxyl groups. NMR determinations indicated the presence of the methylene bridge and the hydroxymethyl function. Neutral equivalent determinations for the solid product was found to be 155, substantially in agreement with the theoretical value of 158 for the expected novel diphenylmethanes herein ($C_{17}H_{16}O_6$). Carbon and hydrogen analysis was found to be 64.9 percent carbon and 5.31 percent hydrogen, substantially in agreement with theoretical values of 64.55 percent carbon and 5.10 percent hydrogen, respectively. On the basis of the structure of the dilactone charge and the above analysis, the presence of the following diphenylmethanes is shown: 3,3'-dicarboxy, 4,4'-di(hydroxymethyl), diphenylmethane, 4,4'-dicarboxy, 3,3'-di(hydroxymethyl), diphenylmethane and 4,3'-dicarboxy, 3,4'-di(hydroxymethyl), diphenylmethane. This result was further confirmed by $^{13}C$ NMR spectroscopy.

EXAMPLE II

Example I was repeated using the dilactone mixture from a run comparable to Example I. A total of 23 grams of lactone mixture (recrystallized from ethyl acetate) was used with 100 milliliters of 10 percent aqueous potassium hydroxide in place of the sodium hydroxide. Reaction temperature was maintained at 50° to 60° C. for one hour. A total of 22.1 grams of material was recovered, amounting to a yield of 85 percent. When this material was subjected to NMR studies and neutral equivalent determinations, values substantially identical to those of Example I were obtained. This shows that the novel diphenylmethanes claimed herein were identical in each example.

The novel isomeric dicarboxy, di(hydroxymethyl) diphenylmethanes of this invention can be used in various conventional applications that are well known for ortho-hydroxymethylbenzoic acid, for example, in reactions with phenols and isocyanates to prepare aryl ethers and carbamates. In this respect, see E. K. Fields, J. Chem. Soc. 4074 (1964). Another use for the novel compounds herein is in the preparation of plastics and coatings in accordance with the procedure disclosed in J. Indian Chem. Soc., Volume 49, No. 12, page 1201 (1972), wherein 3,3'-dicarboxy-2,2'-dihydroxydiphenylmethane has been used in the preparation of condensation polymers. The following example shows the preparation of a polymer using the novel dicarboxy, di(hydroxymethyl) diphenylmethanes herein and ethylene diamine.

EXAMPLE III

A total of seven grams of a mixture of dicarboxy, di(hydroxymethyl) diphenylmethanes from Example I and 50 grams of ethylene diamine were charged into a flask. This mixture was heated for seven days while stirring under a nitrogen atmosphere. Most of the excess ethylene diamine was stripped off from the reaction mixture at atmospheric pressure and final traces were removed under vacuum. The residue, amounting to 8.2 grams. was a light brown solid having a softening point of 250° C. Analysis of the product indicated the reaction proceeded as follows:

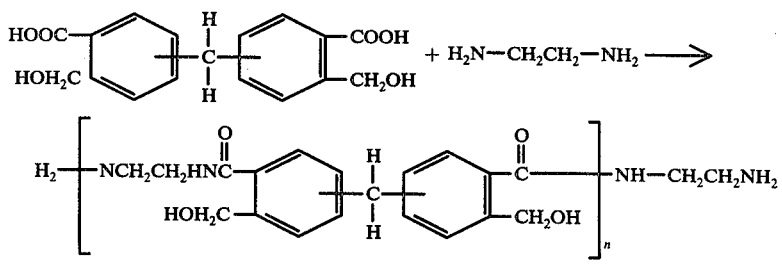

The resin was found to have a molecular weight in excess of 10,000 and distinguished itself by its virtual insolubility in conventional solvents, such as methanol, acetone, ethyl acetate, tetrahydrofuran and benzene. The molten resin was drawn into flexible fibers capable of being cold drawn to impart additional mechanical strength thereto suitable for the preparation of fabrics.

Obviously, many modifications and variations of the invention, as hereinabove set forth, can be made without departing from the spirit and scope thereof, and therefore only such limitations should be imposed as are indicated in the appended claims.

We claim:

1. Diphenylmethanes selected from the group consisting of 3,3'-dicarboxy, 4,4'-di(hydroxymethyl), diphenylmethane, 4,4'-dicarboxy, 3,3'-di(hydroxymethyl), diphenylmethane and 4,3'-dicarboxy, 3,4'-di(hydroxymethyl) diphenylmethane.

2. 3,3'-dicarboxy, 4,4'-di(hydroxymethyl), diphenylmethane.

3. 4,4'-dicarboxy, 3,3'-di(hydroxymethyl), diphenylmethane.

4. 4,3'-dicarboxy, 3,4'-di(hydroxymethyl), diphenylmethane.

* * * * *